US009447495B2

(12) United States Patent
Suzuki et al.

(10) Patent No.: US 9,447,495 B2
(45) Date of Patent: Sep. 20, 2016

(54) CHEMICAL VAPOR DEPOSITION RAW MATERIAL CONTAINING ORGANIC NICKEL COMPOUND, AND CHEMICAL VAPOR DEPOSITION METHOD USING THE CHEMICAL VAPOR DEPOSITION RAW MATERIAL

(71) Applicant: TANAKA KIKINZOKU KOGYO K.K., Tokyo (JP)

(72) Inventors: Kazuharu Suzuki, Tsukuba (JP); Masayuki Saito, Tsukuba (JP); Ryosuke Harada, Tsukuba (JP); Shunichi Nabeya, Tsukuba (JP); Satoshi Miyazaki, Tsukuba (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 14/890,485

(22) PCT Filed: Dec. 27, 2013

(86) PCT No.: PCT/JP2013/085069
§ 371 (c)(1),
(2) Date: Nov. 11, 2015

(87) PCT Pub. No.: WO2014/188629
PCT Pub. Date: Nov. 27, 2014

(65) Prior Publication Data
US 2016/0115587 A1    Apr. 28, 2016

(30) Foreign Application Priority Data

May 22, 2013   (JP) .................. 2013-108030

(51) Int. Cl.
*C23C 16/18*   (2006.01)
*C07F 15/00*   (2006.01)
*C07F 15/04*   (2006.01)

(52) U.S. Cl.
CPC ............... *C23C 16/18* (2013.01); *C07F 15/04* (2013.01)

(58) Field of Classification Search
CPC ................................ C07F 15/04; C23C 16/18
USPC ..................... 556/140, 143; 427/252, 255.28
See application file for complete search history.

(56) References Cited

U.S. PATENT DOCUMENTS 3,121,729 A * 2/1964 Fischer ............... B01J 31/2295
                                                      44/361

FOREIGN PATENT DOCUMENTS

| JP | 2005-093732 | 4/2005 |
| JP | 2006-045649 | 2/2006 |
| WO | WO 2009-081797 | 7/2009 |
| WO | WO 2010-032673 | 3/2010 |

OTHER PUBLICATIONS

Kang, J. et al., "Metalorganic chemical vapor deposition of nickel films from $Ni(C_5H_5)_2/H_2$", J. Mater, Res., vol. 15, No. 8, Aug. 2000, © 2000 Materials Research Society, pp. 1828-1833.
Ishikawa, M. et al., Ni Precursor for Chemical Vapor Deposition of NiSi, Japanese Journal of Applied Physics, vol. 43, No. 4B, 2004, pp. 1833-1836, © 2004 The Japan Society of Applied Physics.
Kada, T. et al., "Volatile CVD precursor for Ni film: cyclopentadienylallylnickel", Journal of Crystal Growth 275 (2005) pp. e1115-e1119.
Lehmkuhl, et al., ($\eta^3$-Cycloalkenyl) ($\eta^5$-cyclopentadienyl) nickel-Komplexe, Chem. Ber. 1984.01, vol. 117, pp. 376-382.
Pasynkiewicz, S., "Hydrogen elimination in cyclopentadienylnickel compounds as a route to organonickel and organic compounds", J. Org. Chem., Sep. 20, 1995, vol. 500, pp. 283-288.
Schnieder, J. et al., "Crystal and molecular structure of (Tri-tert-butyl-$\eta^5$-cyclopentadienyl)—(1,2,4-tri-tert-buty-$\eta^3$-cyclopentenyl) nickel", Chem. Ber., Apr. 1992, vol. 125, No. 4, pp. 843-845.
V.S. Protopopova et al., Chemical Vapor Desposition of Ni—C Films from Bis-(Ethylcyclopentadienyl) Nickel, Journal of Nanoscience and Nanotechnology, vol. 11, 8259-8263, 2011.

* cited by examiner

*Primary Examiner* — Porfirio Nazario Gonzalez
(74) *Attorney, Agent, or Firm* — Orrick Herrington & Sutcliffe, LLP

(57) ABSTRACT

The present invention provides a chemical vapor deposition raw material, which has a low melting point, has heat stability such that no thermal decomposition occurs during vaporization, readily decomposes at low temperature during film-formation, and can stably form a nickel thin-film having fewer impurities. The present invention relates to a chemical vapor deposition raw material containing an organic nickel compound, in which a cyclopentadienyl group or a derivative thereof is coordinated to nickel, and a cycloalkenyl group having one allyl group or a derivative thereof is coordinated to the carbon skeleton of cycloalkyl. This raw material has a low melting point, proper heat stability and film-formation ability at low temperature. Further, due to a high vapor pressure, the raw material is suitable for a three-dimensional electrode material having a three-dimensional structure.

3 Claims, 4 Drawing Sheets

CROSS SECTION OF PORED SUBSTRATE

← SUBSTRATE SURFACE

← CENTER

← BOTTOM

SUBSTRATE SURFACE

CENTER

BOTTOM

CHEMICAL VAPOR DEPOSITION RAW MATERIAL CONTAINING ORGANIC NICKEL COMPOUND, AND CHEMICAL VAPOR DEPOSITION METHOD USING THE CHEMICAL VAPOR DEPOSITION RAW MATERIAL

TECHNICAL FIELD

The present invention relates to a chemical vapor deposition raw material containing an organic nickel compound for producing a nickel thin-film or a nickel compound thin-film by a chemical vapor deposition method (CVD method) or an atomic layer vapor deposition method (ALD method). Specifically, the present invention relates to a chemical vapor deposition raw material which has a low melting point, has proper heat stability such that it does not thermally decompose during vaporization, readily decomposes at low temperature under the film-formation conditions, and can form a nickel thin-film having fewer impurities.

BACKGROUND ART

As a material for forming a field effect transistor (FET) incorporated in an integrated circuit, a nickel (Ni) electrode capable of manufacturing a fine electrode having low resistance has been used. Further, by addition of platinum (Pt) to a nickel electrode, a Ni—Pt electrode with improved heat stability is put to practical use. Meanwhile, a three-dimensional electrode with a three-dimensional structure, which can secure the surface area of an electrode, is expected to be developed in accordance with the refining of the FET. For manufacturing a three-dimensional electrode, an electrode thin-film with uniform and same ratio while having a three-dimensional shape is required to be formed. As a method that satisfies such a requirement, a chemical vapor deposition method such as a CVD method can be used. Since a nickel thin-film or a nickel compound thin-film has film-formation characteristics such as a step coverage (step coverage characteristic) suitable for a three-dimensional electrode by a CVD method, a nickel electrode is highly useful.

For manufacturing a nickel electrode according to a CVD method, as a raw material, many organic nickel compounds are conventionally known. For example, there are provided bis(cyclopentadienyl)nickel $Ni(Cp)_2$ (Non-Patent Document 1), bis(methyl-cyclopentadienyl) nickel $Ni(Me-Cp)_2$ (Non-Patent Document 2), bis(ethyl-cyclopentadienyl)nickel $Ni(Et-Cp)_2$ (Non-Patent Document 3), and (propenyl)(cyclopentadienyl)nickel $Ni(Cp)(C_3H_5)$ (Patent Document 1 and Non-Patent Document 4), but they do not have the above-described required performances, that is, the characteristics that it has a low melting point, has proper heat stability such that it does not thermally decompose at the time of vaporization, readily decomposes at low temperature under the film-formation conditions, and can form a nickel thin-film having fewer impurities.

[Chemical Formula 1]

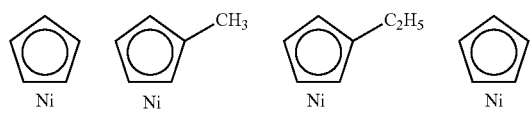

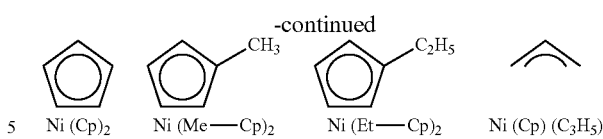

In other words, $Ni(Cp)_2$ having two cyclopentadienyl groups disclosed in Non-Patent Document 1 has a high melting point (173° C.) and a high decomposition temperature. $Ni(Me-Cp)_2$ disclosed in Non-Patent Document 2, in which each of the two cyclopentadienyl groups has one methyl substituent, or $Ni(Et-Cp)_2$ disclosed in Non-Patent Document 3, having an ethyl group instead of a methyl group, has a low melting point, but impurities mix in the prepared Ni film. Further, $Ni(Cp)(C_3H_5)$ disclosed in Patent Document 1 and Non-Patent Document 4, in which one of cyclopentadienyl groups coordinated to nickel is substituted with propenyl having a linear allyl group, has also a low melting point and the characteristics suitable for a raw material for CVD having high vapor pressure, but the Ni film prepared with this compound also tend to be contaminated with impurities.

RELATED ART DOCUMENT

Patent Documents

Patent Document 1: JP 2005-93732 A

Non-Patent Documents

Non-Patent Document 1: J.-K. Kang and S.-W. Rhee, J. Mater. Res., 2005, 15(8), 1828.
Non-Patent Document 2: M. Ishikawa, T. Kada, H. Machida, Y. Ohshita and A. Ogura, Jpn. J. Appl. Phys., 2004, 43(4B), 1833.
Non-Patent Document 3: S. E. Alexandrov and V. S. Protopopova, J. Nanosci. Nanotechnol., 2011, 11(9), 8259.
Non-Patent Document 4: T. Kada, M. Ishikawa, H. Machida, A. Ogura, Y. Ohshita and K. Soai, J. Cryst. Growth, 2005, 275, e1115.

SUMMARY OF THE INVENTION

Problems to be Solved by the Invention

Against the above-described background, the present invention provides a chemical vapor deposition raw material, which has, in balance, the performances required for a CVD compound, that is, the characteristics that: it has a low melting point; it does not thermally decompose at the time of vaporization and it allows all the raw materials to vaporize; it readily decomposes at low temperature under the film-formation conditions; and it can stably form a highly pure nickel thin-film.

Means for Solving the Problems

To solve the above problem, the present invention relates to a chemical vapor deposition raw material for preparing a nickel thin-film or a nickel compound thin-film by a chemical vapor deposition method, comprising an organic nickel compound in which a cyclopentadienyl group (Cp) or a derivative thereof is coordinated to nickel and a cycloalkenyl group having one allyl group or a derivative (X) thereof is coordinated to a carbon skeleton of cycloalkyl, having a following formula. Note that substituents $R_1$ to $R_5$ each independently represent values, which may be the same or different from each other.

The chemical vapor deposition method of the present invention should cover both a chemical vapor deposition method (CVD method) and an atomic layer vapor deposition method (ALD method).

[Chemical Formula 2]

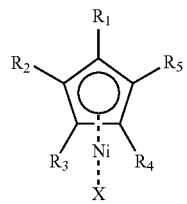

(In the formula, X respressents a cycloalkenyl group having one allyl group in the carbon skeleton of cycloalkyl, $R_1$ to $R_5$ represent $C_nH_{2n+1}$, n represents 0 to 6, and n is an integer.)

The chemical vapor deposition raw materials of the present invention have cycloalkenyl along with cyclopentadienyl, as a ligand. As in the present invention, the nickel compound coordinated with a cycloalkenyl group (X) along with a cyclopentadienyl group (Cp) may realize stable vaporization since it hardly thermally decomposes at the vaporization stage of a raw material (about 80° C.) as a chemical vapor deposition raw material. The heat stability improves as described above, and a decomposition reaction progresses quickly at low temperature (about 200° C.) at the nickel film-formation stage after the vaporization in the present raw materials.

Cycloalkenyl has the structure in which, as a complex structure, an allyl group, that is, three carbon atoms of 2-propenyl ($CH_2$=CH—$CH_2$—) are equivalently coordinated for nickel. It is believed that the structure having the allyl group in the carbon skeleton of monocyclic hydrocarbon enables an allyl group to be stably coordinated to nickel to contribute to the stabilization of the compound at the vaporization stage and the like.

As a cycloalkenyl group or a derivative (X) thereof, any one type among cyclobutenyl, cyclopentenyl, cyclohexenyl, cycloheptenyl, cyclooctenyl, cyclononenyl, or derivatives thereof, having a following formula 3, is preferable. Particularly, as a carbon number of carbon skeleton, 5 or 6, that is, cyclopentenyl ($C_5H_7$) or cyclohexenyl ($C_6H_9$), is preferable. This is because the raw material vaporizes stably during the vaporization stage, and readily decomposes at low temperature during the film-formation stage.

[Chemical Formula 3]

X =

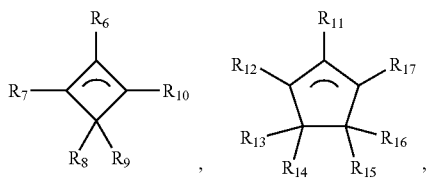

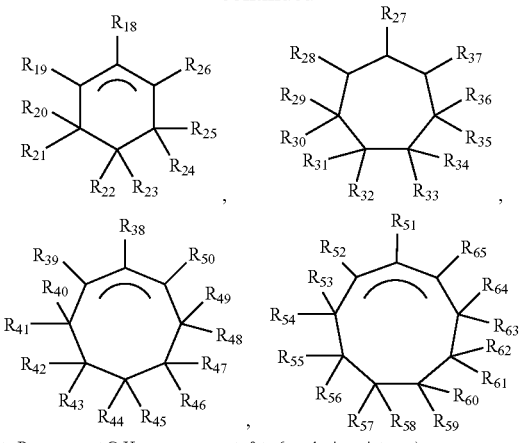

($R_6$ to $R_{65}$ represent $C_nH_{2n+1}$, n represents 0 to 6, and n is an integer.)

For a cycloalkenyl group or a derivative (X) thereof, preferably, among the substituents ($R_6$ to $R_{65}$) of side chains, all of them are hydrogen atoms, one or two of them are alkyl groups, and all the rest, substituents, are hydrogen atoms. The substituents ($R_6$ to $R_{65}$) have carbon number (n) of 1 to 6, preferably 1 to 4. $R_6$ to $R_{65}$ each independently have the substituent of carbon number, which may be the same or different from each other. When as the substituents ($R_6$ to $R_{65}$), the number of alkyl substituents with respect to a hydrogen atom are too large or the carbon chain of alkyl substituent is too long, the melting point tends to be higher and vapor pressure tends to be lower. Further, a boiling point becomes higher and impurities are easily mixed in a nickel film.

Further, all the substituents ($R_1$ to $R_5$) of cyclopentadienyl (Cp) being another ligand may be a hydrogen atom, or the cyclopentadienyl (Cp) may be the derivative obtained by substitution of an alkyl group. As a derivative of cyclopentadienyl, the derivative, in which one of the substituents ($R_1$ to $R_5$) is an alkyl group and the rest, four substituents, are a hydrogen atom, is preferable. Further, the carbon number of the substituents ($R_1$ to $R_5$) is 1 to 6, preferably 1 to 4. When the substituent of cyclopentadienyl is too long, there are tendencies that the melting point of an organic nickel compound increases, the vapor pressure reduces according to the increase in molecular weight, and it hardly vaporizes and thereby impurities are mixed in a film at the time of forming the film, and it is difficult to maintain proper characteristics as a chemical vapor deposition raw material.

The chemical vapor deposition raw material according to the present invention is useful for forming a nickel thin-film by a chemical vapor deposition method. For the chemical vapor deposition method, the nickel compound as a raw material is heated and vaporized under vacuum to generate a raw material gas. In this method, a complex is thermally decomposed with such a raw material gas sprayed on the heated surface of a substrate to form the nickel thin-film, and the above-described raw materials are used as an organic nickel compound.

The heating temperature of a film-formation can be set to 100 to 300° C. Since one of the objects of the present invention is to lower the film-formation temperature, the heating temperature is preferably 130 to 250° C., and more preferably 150 to 200° C. When the heating temperature is lower than 100° C., it is difficult to perform a film-formation reaction and to obtain the desired thickness of a film. When the heating temperature is too high, it is difficult to form a uniform thin-film on a three-dimensional electrode, and thus at the time of forming a nickel film, impurities are easily mixed in the film.

Advantageous Effects of the Invention

The chemical vapor deposition raw material of the present invention has a low melting point, proper heat stability, and can form a film at low temperature. Further, since the vapor pressure is high, it is suitable for forming the film on a three-dimensional surface, and thus suitable as a three-dimensional electrode material.

DESCRIPTION OF EMBODIMENTS

Figure 1:
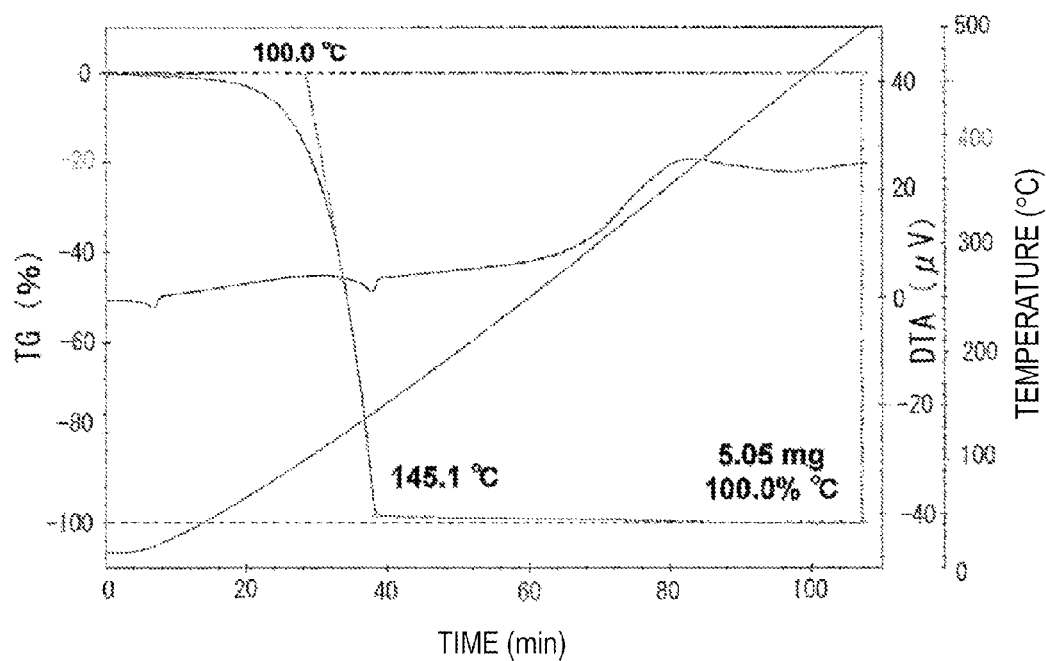
FIG. 1 illustrates a result of measuring the TG-DTA of a compound of Example 2.

Hereinafter, the preferred embodiments of the present invention will be described.

For the present embodiment, four organic nickel compounds having following formulas were prepared, and the heat stability and film-formation test were performed. Further, the performance of the formed thin-film was evaluated. Note that, for preparing a nickel compound, the preparing method disclosed in Non-Patent Document 5 was referred to.

[Non-Patent Document 5] H. Lehmkuhl, A. Rufinska, C. Naydowski and R. Mynott, Chem. Ber., 1984, 117, 376.

[Chemical Formula 4]

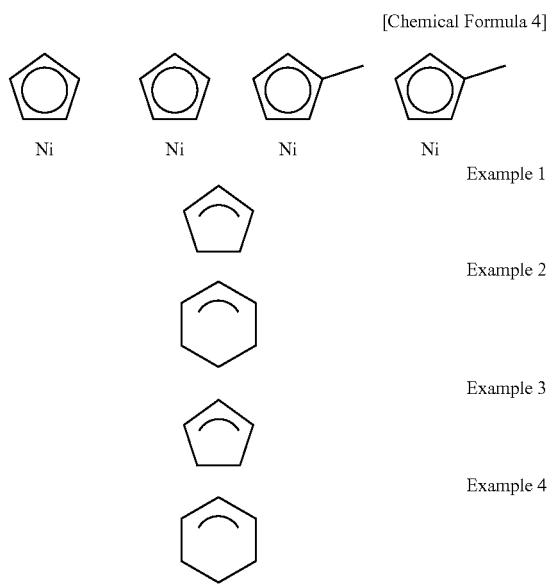

Example 1

By the following processes, ($\eta^3$-cyclopentenyl)($\eta^5$-cyclopentadienyl)nickel (II) was prepared. 120 mL of diethyl ether and 40 mL of tetrahydrofuran were added to a three-neck flask with 20.0 g (106 mmol) of nickelocene, and 9.1 g (138 mmol) of cyclopenta 1,3-diene was further added thereto. 59.0 mL of propyl magnesium chloride was dropped using a dropping funnel while the solution thus obtained was cooled at 0° C.; then, the temperature of the solution was turned to a room temperature; and the solution was stirred for 70 hours. After the reaction was completed, the solvent was vacuum-distilled, and 200 mL of pentane was added to the residue for extraction. The extract thus obtained was filtered through an active alumina, and the solvent of the filtrate was vacuum-distilled. The residue was sublimated to obtain 7.24 g (37.9 mmol) of a dark purple-red needle crystal. The yield was 36%.

Example 2

By the following processes, ($\eta^3$-cyclohexenyl)($\eta^5$-cyclopentadienyl)nickel (II) was prepared. 120 mL of diethyl ether and 40 mL of tetrahydrofuran were added to a three-neck flask with 20.0 g (106 mmol) of nickelocene, and 11.0 g (138 mmol) of cyclopenta 1,3-diene was further added thereto. 59.0 mL of propyl magnesium chloride solution (2.0 M, diethyl ether solution) was dropped using a dropping funnel while the solution thus obtained was cooled at 0° C.; then, the temperature of the solution was turned to a room temperature; and the solution was stirred for 48 hours. After the reaction was completed, the solvent was vacuum-distilled, and 200 mL of pentane was added to the residue for extraction. The extract thus obtained was filtered through an active alumina, and the solvent of the filtrate was vacuum-distilled. The residue was vacuum-distilled to obtain 8.84 g (43.3 mmol) of dark purple solution. The yield was 41%.

Example 3

By the following processes, ($\eta^3$-cyclopentenyl)(methyl-$\eta^5$-cyclopentadienyl)nickel (II) was prepared. 120 mL of diethyl ether and 40 mL of tetrahydrofuran were added to a three-neck flask with 23.0 g (106 mmol) of dimethylnickelocene, and 9.1 g (138 mmol) of cyclopenta 1,3-diene was further added thereto. 59.0 mL of propyl magnesium chloride was dropped using a dropping funnel while the solution thus obtained was cooled at 0° C.; then, the temperature of the solution was turned to a room temperature; and the solution was stirred for 70 hours. After the reaction was completed, the solvent was vacuum-distilled, and then 200 mL of pentane was added to the residue for extraction. The extract thus obtained was filtered through an active alumina, and then the solvent of the filtrate was vacuum-distilled. The residue was sublimated to obtain 6.52 g (31.8 mmol) of a dark purple-red needle crystal. The yield was 30%.

Example 4

By the following processes, ($\eta^3$-cyclohexenyl)(methyl-$\eta^5$-cyclopentadienyl)nickel (II) was prepared. 120 mL of diethyl ether and 40 mL of tetrahydrofuran were added to a three-neck flask with 23.0 g (106 mmol) of dimethylnickelocene, and 11.0 g (138 mmol) of cyclohexa 1,3-diene was further added thereto. 59.0 mL of propyl magnesium chloride solution (2.0 M, diethyl ether solution) was dropped using a dropping funnel while the solution thus obtained was cooled at 0° C.; then, the temperature the solution was turned to a room temperature; and the solution was stirred for 48 hours. After the reaction was completed, the solvent was vacuum-distilled, and then 200 mL of pentane was added to the residue for extraction. The extract thus obtained was filtered through an active alumina, and then the solvent of the filtrate was vacuum-distilled. The residue thus obtained was vacuum-distilled to obtain 8.00 g (36.5 mmol) of dark purple solution. The yield was 35%.

For the compound of Example 2, the thermal characteristics were evaluated by TG-DTA and DSC.

Thermal Decomposition Characteristics (TG-DTA):

In the analysis, using TG-DTA2000SA manufactured by Bruker-AXS, the weight change of a sample was observed when 5 mg of the nickel compound of Example 2 was heated at the temperature rising rate of 5° C./min from about 24° C. to 500° C. under a nitrogen air current (200 mL/min). The measuring result of Example 2 is illustrated in FIG. 1.

The decrease in weight of the compound of Example 2 started at 100.0° C., and stopped at 145.1° C. When the weight loss rate was 100.0%, all the samples were evaporated. From the above, it was confirmed that when the compound was used in a chemical vapor deposition method, at the time of evaporating raw materials (a low temperature of 150° C. or lower), all the samples can be evaporated without thermal decomposition.

Calorimetry (DSC):

The compound of Example 2 (2 mg of sample weight) was filled in a pressure-resistant cell made of stainless steel in DSC-220C manufactured by Seiko Instruments Inc., and the change in calorie was observed at the measurement temperature range of 0 to 400° C. at the temperature rising rate of 10° C./min under a nitrogen atmosphere.

As the result of DSC measurement, the melting point was 25° C., and exothermic reaction was observed at 199° C. by the decomposition. Therefore, it was confirmed that the composition easily liquefied and was stable that did not decompose until about 200° C. In contrast, the raw material of Non-Patent Document 1 had the melting point of 173° C., and the thermal decomposition of the raw material started as soon as it melted. Non-Patent Document 1 discloses that there is the exothermic peak by the decomposition at 186° C. From the above, it was found that the compound of Example 2 had higher heat stability than that of the nickel compound disclosed in Non-Patent Document 1.

Film-Formation Test:

With the compound of Example 2 as a raw material, a nickel thin-film was formed by a CVD method using a cold wall-typed film-formation device. For a substrate to be formed with a thin-film, silicon or oxidation silicon was used. The film-formation conditions were as follows. Further, for bis(cyclopentadienyl)nickel $Ni(Cp)_2$ disclosed in Non-Patent Document 1, a nickel thin-film was formed in the same conditions.

[Conditions for Forming Nickel Thin-Film]
Sample-heating temperature: 80° C.
Substrate-heating temperature: 170 to 200° C.
Carrier gas: nitrogen, 30 sccm
Reaction gas: hydrogen, 50 sccm
Pressure: 13,000 Pa
Film-formation time: 5 to 60 minutes For the Ni film prepared as described above, the characteristic tests such as the following SEM observation and specific resistance were performed.

Figure 2:
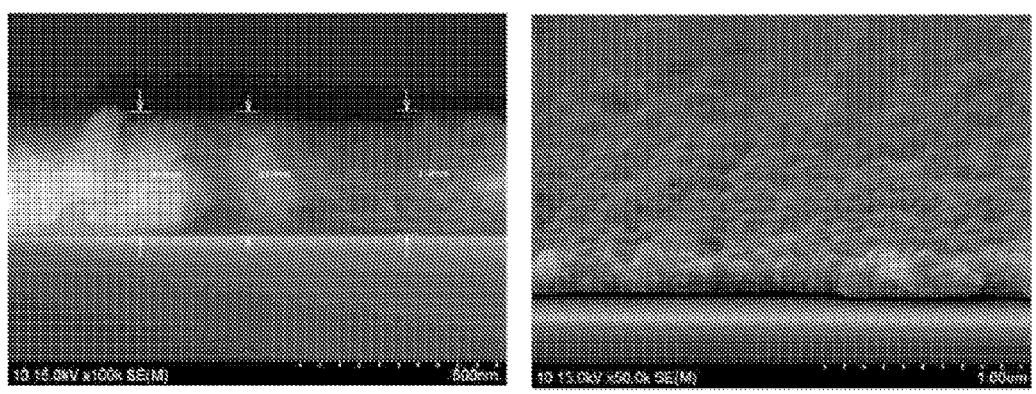
FIG. 2 is a SEM observation micrograph showing a nickel thin-film prepared with use of the compound of Example 2.
Figure 3:
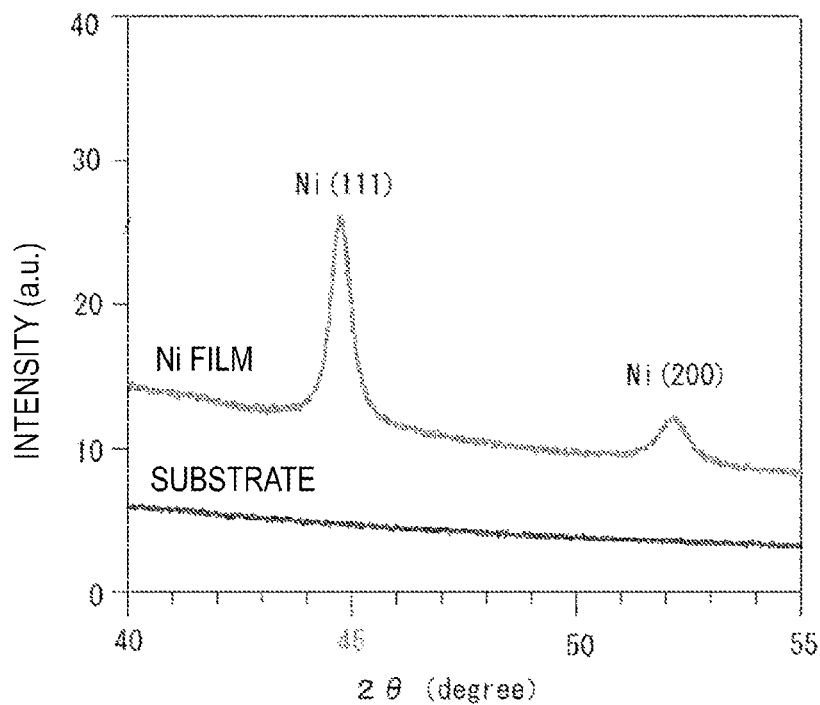
FIG. 3 illustrates a result of measuring the XRD of the nickel thin-film prepared using the compound of Example 2.

[SEM Observation (FIG. 2)]

The Ni film had a thickness of 200 to 350 nm, and was a uniform and continued film (Example 2). There were observed no cracks, holes, or island-like aggregates.

[Specific Resistance]

The result of measuring specific resistance was 22 $\mu\Omega$cm (Example 2). This value was close to the value of the specific resistance (7 $\mu\Omega$cm) of a nickel simple substance. In contrast, the specific resistance of the Ni film prepared by the Ni compound of Non-Patent Document 1 was at least 30 $\mu\Omega$cm. From the above, it was confirmed that the specific resistance of the Ni film formed with the raw material of Example 2 was low.

[XRD (FIG. 3)]

The diffraction peaks of the side (111) and side (200) derived from Ni were observed (Example 2), and formation of a metal nickel film was confirmed.

Figure 4:
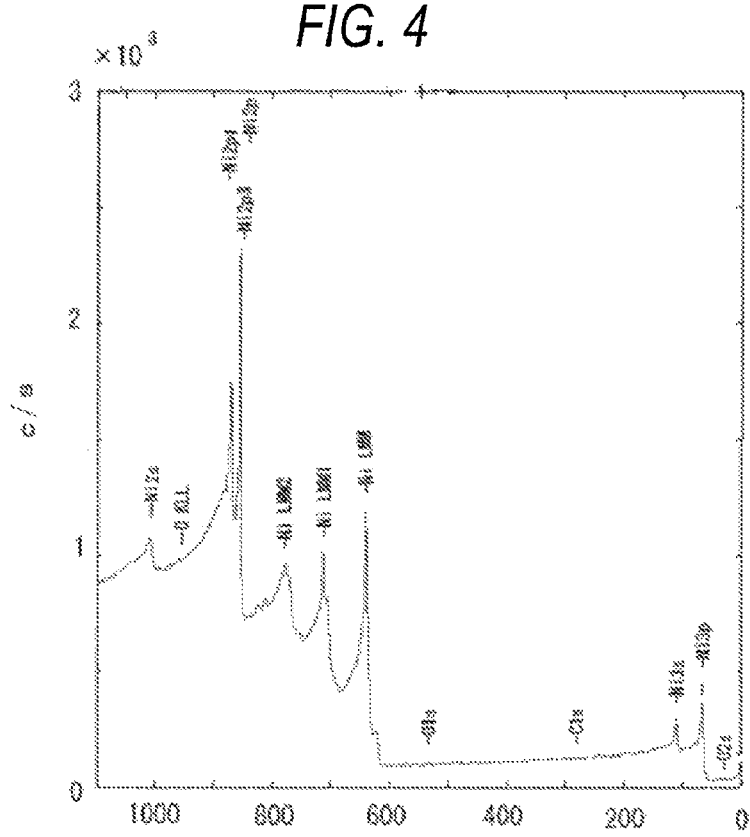
FIG. 4 illustrates a result of measuring the XPS of the nickel thin-film prepared using the compound of Example 2.

[XPS (FIG. 4 and Table 1)]

For Ni film, the purity was 99.5 wt %, and the content of carbon was 0.1 wt % or less (Example 2). In contrast, for the Ni film prepared in the same conditions using $Ni(Cp)_2$ disclosed in Non-Patent Document 1, the purity was 98.7 wt % and the content of carbon was 0.5 wt %. From the above-described results, it was confirmed that the purity of the Ni film prepared with the compound of Example 2 was high.

TABLE 1

|  | C | O | Ni |
|---|---|---|---|
| Example 2 | 0.1 wt % | 0.4 wt % | 99.5 wt % |
| Ni $(Cp)_2$ | 0.5 wt % | 0.8 wt % | 98.7 wt % |

[Step Coverage Rate]

The Ni film was formed in the same conditions as the above-described film-formation test, except that the substrate, in which the surface was SiN, which has pores (aspect ratio of 40) with the diameter of 200 nm and the depth of 8,000 nm, and the surface of the pore part was $SiO_2$, was used, the substrate temperature was 200° C., and the film-formation time was 15 minutes.

Figure 5:
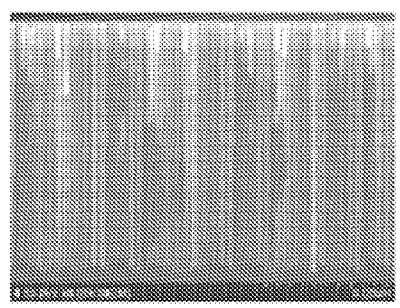
FIG. 5 shows a result (SEM) of a film-formation test in pores by the compound of Example 2.
Figure 5:
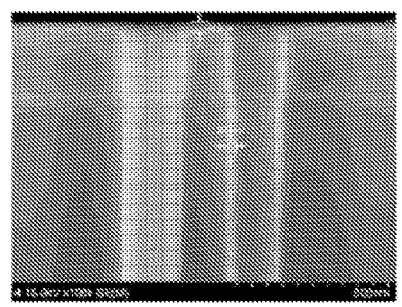
Figure 5:
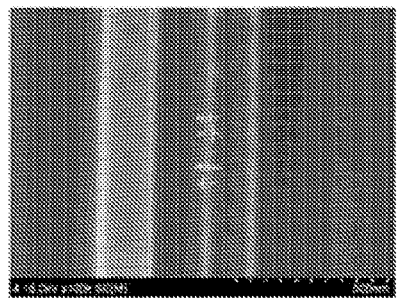
Figure 5:
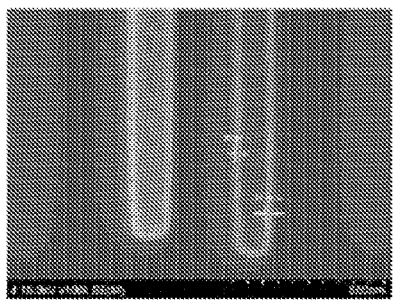

For the Ni film formed as described above, the substrate surface had a film thickness of 33 nm and a specific resistance of 20 $\mu\Omega$m, the center (aspect ratio of 20) had a film thickness of 29 nm and a step coverage rate of 88%, and the bottom (aspect ratio of 40) had a film thickness of 22 nm and a step coverage rate of 67%. From the above-described results and FIG. 5, it was confirmed that the uniform Ni film can be formed to the bottom in the pore having an aspect ratio of 40 using the raw material of Example 2.

[Silicidation Test]

The Ni film prepared on the Si substrate as described above was heated at 500° C. for 10 minutes to alloy Ni and Si (silicide).

Figure 6:
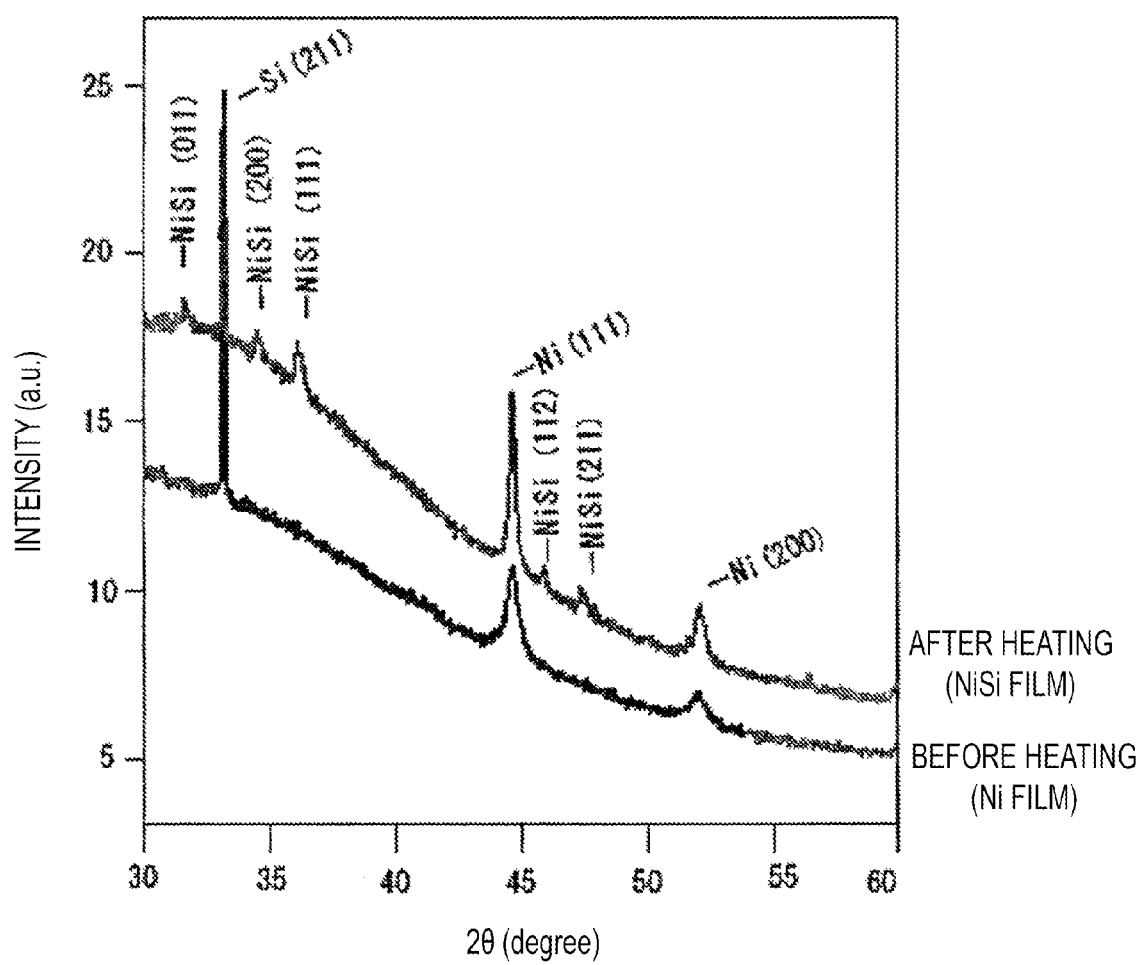
FIG. 6 shows a result (XRD) of a silicidation test of the nickel thin-film prepared using the compound of Example 2.

From FIG. 6, it was confirmed that a diffraction peak derived from NiSi was observed after heating, and thus silicidiation was confirmed.

INDUSTRIAL APPLICABILITY

The raw materials according to the present invention has, in balance, the characteristics required for forming an electrode thin-film by a chemical vapor deposition method, thereby having a low melting point and proper heat stability, and it is possible to form a film at low temperature. Further, due to high vapor pressure, it is also suitable for forming a film on the three-dimensional surface. For this reason, it can also be applied for manufacturing a three-dimensional electrode.

The invention claimed is:

1. A chemical vapor deposition method for forming a nickel thin-film or a nickel compound thin-film on a substrate comprising the steps of: evaporating a raw material containing an organic nickel compound to produce a raw material gas; and heating the raw material gas while the raw material gas is introduced to a surface of the substrate, wherein the chemical vapor deposition raw material comprises an organic nickel compound in which a cyclopentadienyl group (Cp) or a derivative thereof is coordinated to nickel and a cycloalkenyl group having one allyl group or a derivative (X) thereof is coordinated to a carbon skeleton of cycloalkyl, having a following formula:

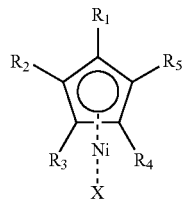

wherein, X is a cycloalkenyl group having one allyl group in the carbon skeleton of cycloalkyl, R1 to R5 independently is CnH2n+1, n being 0 to 6, and n is an integer.

2. The chemical vapor deposition method of claim 1, wherein the cycloalkenyl group or the derivative (X) thereof is one of cyclobutenyl, cyclopentenyl, cyclohexenyl, cycloheptenyl, cyclooctenyl, cyclononenyl, or derivatives thereof, having a following formula:

[Chemical Formula 3]

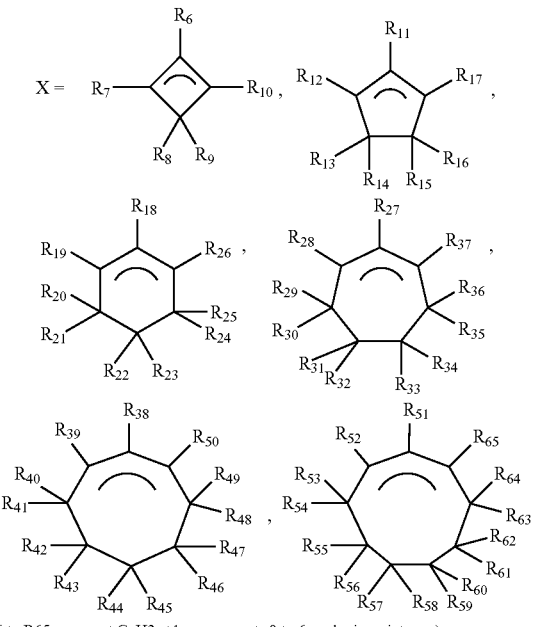

(R6 to R65 represent CnH2n+1, n represents 0 to 6, and n is an integer.).

3. The chemical vapor deposition method of claim 1, wherein for the derivative of cyclopentadienyl (Cp), one of substituents (R1 to R5) of cyclopentadienyl group (Cp) is an alkyl group and the rest, four substituents, are a hydrogen atom.

* * * * *